United States Patent [19]

Sullivan

[11] 4,119,780

[45] Oct. 10, 1978

[54] 2(ISOPROPYLDITHIO)BENZIMIDAZOLE

[75] Inventor: Alfred Bay Sullivan, Wadsworth, Ohio

[73] Assignee: Monsanto Company, St. Louis, Mo.

[21] Appl. No.: 734,996

[22] Filed: Oct. 22, 1976

Related U.S. Application Data

[60] Division of Ser. No. 508,047, Sep. 23, 1974, Pat. No. 4,006,155, which is a continuation-in-part of Ser. No. 266,458, Jun. 26, 1972, Pat. No. 3,859,297, which is a continuation-in-part of Ser. No. 880,893, Nov. 28, 1969, Pat. No. 3,705,923.

[51] Int. Cl.$^2$ ............................................. C07D 235/28
[52] U.S. Cl. ............................ 548/329; 260/306.5; 260/302 E; 260/302 F; 260/302 H; 260/302 S; 260/306; 260/306.6 A; 260/306.7 T; 260/306.8 F; 260/306.7 E; 260/307 D; 260/304 R; 260/934; 544/232
[58] Field of Search ...................... 260/309.2; 548/329

[56] References Cited

U.S. PATENT DOCUMENTS

| 3,258,463 | 6/1966 | Price et al. | 260/251 |
| 3,974,170 | 8/1976 | Campbell et al. | 260/309.2 |

OTHER PUBLICATIONS

Oda, "Chemical Abstracts", vol. 81, 1974, Col. 79124 (Abstract of Japan Patent 73-103, 639, Patented 12/26/73).

Angelini, "Chemical Abstracts", vol. 49, 1955, Col. 116276 (Abstract of Ann. Chim. (Rome), vol. 45 (1955), pp. 162–165).

Sirakwa, et al., Chem. Pharm. Bull., vol. 18 (2), 1970, pp. 235–242.

*Primary Examiner*—Donald G. Daus
*Assistant Examiner*—James H. Turnipseed

[57] ABSTRACT

2(Isopropyldithio)benzimidazole is a potent inhibitor of prevulcanization of vulcanizable rubber compositions.

1 Claim, No Drawings

2(ISOPROPYLDITHIO)BENZIMIDAZOLE

This application is a division of application Ser. No. 508,047, filed Sept. 23, 1974, now U.S. Pat. No. 4,006,155, issued Feb. 1, 1977; which application was a continuation-in-part of application Ser. No. 266,458, filed June 26, 1972, now U.S. Pat. No. 3,859,297, issued Jan. 7, 1975; which application, in turn, was a continuation-in-part of application Ser. No. 880,893, filed Nov. 28, 1969, now U.S. Pat. No. 3,705,923, issued Dec. 12, 1972.

Organic polysulfides have a wide variety of commercial applications such as vulcanization accelerators or vulcanization agents in the curing of rubber and solvent or plasticizers for rubber or plastics. They may also be used as intermediates in the preparation of other organic compounds and as catalysts in addition reactions of olefinic unsaturated compounds. Certain ones are high pressure lubricants, while other biologically active, are useful as fungicides, insecticides, nematocides and bacteriocides.

It is known that symmetrical organic disulfides may be produced by reaction of an organic chloride with sodium disulfide, by catalytic oxidation of a mercaptan using hydrogen peroxide and cupric chloride catalyst; by the reaction of elemental sulfur in the presence of a Friedel-Crafts catalyst with dialkyl sulfide, or by reaction of a mercaptan with sulfur under basic conditions. It is difficult to produce pure disulfides from reaction with sulfur because of formation of polysulfides. A process for converting organo-sulfenyl chlorides to disulfides is also known. In all the above-mentioned processes, only symmetrical disulfides can be produced.

Asymmetrical organic disulfides have been produced by heating a mixture of two different symmetrical disulfides in the presence of an alkali sulfide to effect disproportionation or by oxidizing a mixture of two different mercaptans using a metal phthalocyanine catalyst.

One advantage of the present process is that both symmetrical and unsymmetrical organic disulfides or trisulfides may be produced under mild reaction conditions in absence of any catalyst whatsoever. Neither oxidative reagent nor hydroxide is required. The only materials needed are two reactants hereinafter described.

A further advantage is that substantially quantitative yields of essentially pure disulfides and trisulfides are produced by simple procedures; while another is that polysulfides having a wide variety of radicals and physical properties may be prepared. By variation of two simple reactants, it is possible to produce polysulfides having the desired molecular weight, solubility, boiling point, toxicity, or other property desired. The process also may be used in the purification of sour petroleum fractions and as an analytical procedure. These and other advantages will become apparent as the description of the invention proceeds, for example, the ability to recycle the imide formed as a by-product of the reaction.

SUMMARY OF THE INVENTION

According to the present invention, organic polysulfides may be produced by reacting a compound containing one or more —SH radicals with a sulfenamide characterized by the presence of a carbonyl group adjacent to the sulfenamide nitrogen. The characteristic nucleus is

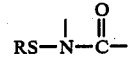

where the dangling valence on the nitrogen may be linked to a second carbonyl, alkyl, aryl, cycloalkyl, hydrogen, alkylene carbon or arylene carbon and R is alkyl, aryl, or cycloalkyl and the dangling valence on the carbonyl may be linked to alkyl, aryl, cycloalkyl, alkylene carbon or arylene carbon, and the unsatisfied dangling valences of the nitrogen and carbonyl radicals are satisfied by forming a heterocyclic ring through a common alkylene or arylene radical.

Sulfenamides of this type are disclosed as prevulcanization inhibitors in the following patent applications; amide, imide and urea sulfenamides are disclosed in Ser. No. 714,445 filed Mar. 20, 1968 now U.S. Pat. No. 3,546,185 issued Dec. 8, 1970; sulfenamides derived from dimercaptans and the above imides are disclosed in Ser. No. 80,815, filed Oct. 14, 1970 which is a division of Ser. No. 704,186, filed Sept. 20, 1967 now abandoned; said application 704,186 is a division of Ser. No. 646,202, filed June 15, 1967 which through continuation application Ser. No. 697,615, Jan. 15, 1968 is now U.S. Pat. No. 3,562,225 issued Feb. 9, 1971; cyclic urea sulfenamides are further disclosed in Ser. No. 696,123, filed Jan. 8, 1968 now U.S. Pat. No. 3,473,667 issued Oct. 21, 1969; and U.S. Pat. No. 3,427,319 issued Feb. 11, 1969; and also the thiosulfenamides are disclosed in Ser. No. 643,401, filed June 5, 1967 now U.S. Pat. No. 3,539,538 issued Nov. 10, 1970. All sulfenamides disclosed therein are hereby incorporated by reference into this application. All the amide, imide and urea sulfenamides disclosed are suitable for the practice of this invention.

Sulfenamides suitable for the practice of this invention include compounds of the formula

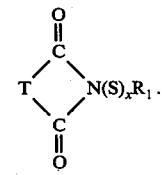

The reaction is represented by equation (I):

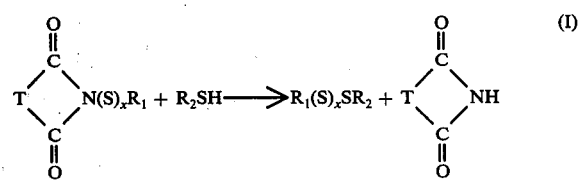

$R_1$ and $R_2$ individually are alkyl, cycloalkyl, aralkyl, alkenyl, aryl, alkaryl, acyl,

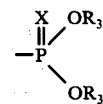

or benzothiazolyl and $x$ is one or two. The $R_1$ and $R_2$ radicals may contain substituents. Suitable substituents are chloro, bromo, fluoro, iodo, hydroxy, alkoxy or nitro, T represents (acyclic or cyclic) aliphatic, olefinic, or aromatic hydrocarbon divalent radicals. Examples of T are alkylene, alkenylene and arylene, such as phenylene.

If a symmetrical polysulfide is desired, then reactants containing similar $R_1$ and $R_2$ groups are selected, otherwise reactants having different $R_1$ and $R_2$ groups are selected. Both di- and trisulfides may be produced by the process. If a disulfide is desired, a monothioimide, meaning that $x$ is one, is selected; when a trisulfide is desired, then a dithioimide, $x$ is two, is selected.

The process is a general one having exceedingly wide applicability. The particular carbonyl thioimide and the nature of the radical attached to —SH are not significant. It appears that all known mercaptans and carbonyl thioimides are useful for the practice of this invention. In general, any compound having one or more —SH groups as the only reactive substituent is a suitable reactant.

Bis($R_1$-polysulfides) may be made by using a dithiol (dimercaptan) instead of a simple mercaptan or by using a bis thioimide and a simple mercaptan. The equations for these reactions are illustrated thusly:

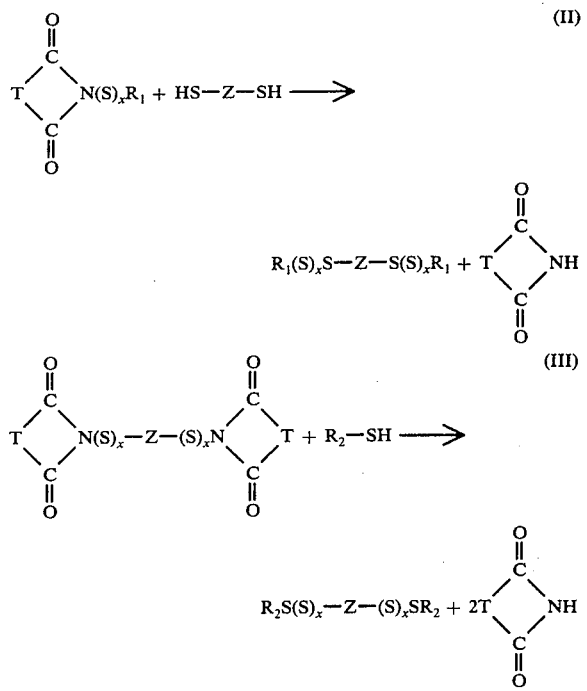

wherein $R_1$, T and $x$ have the same meaning as before. Z is a divalent radical derived by removal ot two hydrogen atoms from (acyclic or cyclic) aliphatic, olefinic or aromatic hydrocarbons. Examples of Z are alkylene, cycloalkylene, alkenylene, cycloalkenylene or arylene. Lower alkylene of two to six carbon atoms or phenylene are the preferred radicals.

The preferred process for the preparation of organic polysulfides comprises reacting a thioimide of the formula:

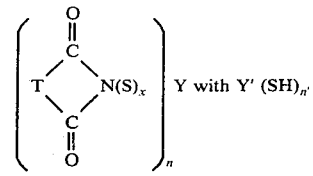

where T is alkylene, cycloalkylene, alkenylene, cycloalkenylene, or arylene, and $n$, $n'$ and $x$ are one or two; when $n$ and $n'$ are one, Y and Y' individually are

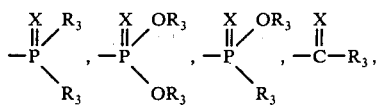

benzothiazolyl or —$R_3$ where $R_3$ is alkyl, cycloalkyl, aralkyl, alkenyl, aryl, or alkaryl; X is oxygen or sulfur; when $n$ or $n'$ is two, Y or Y' respectively is selected from the group represented as T.

The term alkyl means any monovalent radical derived from an aliphatic saturated hydrocarbon by the removal of one hydrogen atom. Their general formula is $C_nH_{2n+1}$. The alkyl radical may be primary, secondary, or tertiary, and any carbon chain attached to the carbon from which the hydrogen is removed may be branched or unbranched. Alkyl radicals of 1–20 carbon atoms are suitable. Lower alkyl radicals of 1–10 carbon atoms are preferred. Cycloalkyl radicals are aliphatic cyclic hydrocarbons of the series $C_nH_{2n-1}$. The preferred cycloalkyl radicals contain 5–8 carbon atoms in the ring but cycloalkyl radicals of 3–12 carbon atoms are suitable. Aralkyl radicals are univalent alkyl radicals having an aryl radical attached to the aliphatic hydrocarbon chain. Preferred aralkyl radicals are benzyl, 1-phenethyl, 2-phenethyl, 2-phenylpropyl and 2-phenyl-2-propyl.

Alkenyl means a monovalent radical derived from an aliphatic unsaturated hydrocarbon by the removal of one hydrogen atom. Alkenyl belongs to the series $C_nH_{2n-1}$ and contains one double bond. Lower alkenyl radicals of 3–10 carbon atoms are preferred. Cycloalkenyl is a monovalent radical derived from an aliphatic cyclic unsaturated hydrocarbon by the removal of one hydrogen atom. Cycloalkenyl belongs to the series $C_nH_{2n-3}$ and contains one double bond. Lower cycloalkenyl radicals of 5 to 8 carbon atoms are preferred.

Aryl is a monovalent organic radical, the free valence of which belongs to an aromatic carbocyclic nucleus and not to a side chain. Phenyl, naphthyl and anthracenyl are examples. Alkaryl radicals are aryl radicals as described having lower alkyl radicals attached to the carbocyclic chain, examples of which are tolyl, xylyl, cumenyl and p-t-butylphenyl.

Acyl is an organic radical derived from an organic acid by removal of the hydroxyl group. This radical may be represented by the formula

$$\overset{X}{\underset{\|}{AC-}}$$

where X is sulfur or oxygen and A is alkyl, aralkyl, cycloalkyl, aryl or alkaryl. A is preferably aryl, for example, benzoyl.

The term alkylene means any divalent radical derived from an aliphatic saturated hydrocarbon by the removal of two hydrogen atoms and has the general formula $C_nH_{2n}$. Lower alkylene radicals of 2–6 carbon atoms are preferred. Cycloalkylene is a divalent radical derived by removal of an additional hydrogen atom from a cycloalkyl radical. The general formula for cycloalkylenes is $C_nH_{2n-2}$. Cycloalkylenes of 5–8 carbon atoms are preferred.

Alkenylene means a divalent radical derived from an aliphatic unsaturated hydrocarbon by the removal of two hydrogen atoms. Alkenylene belongs to the series $C_nH_{2n-2}$ and contains one double bond. Lower alkenylene radicals of 2 to 10 carbon atoms are preferred. Cycloalkenylene means a divalent radical derived from removal of an additional hydrogen atom from a cycloalkenyl radical. The general formula for cycloalkenylenes is $C_nH_{2n-4}$ and contains one double bond. Lower cycloalkenylenes of 5 to 8 carbon atoms are preferred.

T is a divalent radical derived from the removal of two hydrogen atoms from (acyclic or cyclic) saturated aliphatic, olefinic, or aromatic hydrocarbon. The radicals are alkylene, aralkylene, cycloalkylene, alkenylene, cycloalkenylene, arylene, and alkarylene. Examples of such radicals are ethylene, propylene, butylene, amylene, hexylene, octylene, cyclobutylene, cyclopentylene, cyclohexylene, cyclooctylene, vinylene, propenylene, phenylene and naphthylene. The heterocyclic radical made by the T group along with the two carbonyl groups and the nitrogen atom is an imido radical. Examples of such imido radicals are succinimidyl, glutarimidyl, adipimidyl, phthalimidyl, maleimidyl and hydrophthalimidyl.

One class of disulfides produced by the subject process is characterized by at least one of the radicals attached to sulfur being phosphoryl with O,O substituted thiophosphoryl a preferred phosphoryl radical with di(lower alkyloxy) thiophosphoryl radicals being especially preferred.

Specific examples of $R_1$ and $R_2$ are methyl, ethyl, propyl, isopropyl, butyl, isobutyl, sec-butyl, tert-butyl, amyl, hexyl, octyl, decyl, dodecyl, hexadecyl, eicosyl, cyclopentyl, cyclohexyl, cyclooctyl, cyclododecyl, benzyl, cumenyl, phenethyl, vinyl, phenyl, allyl, naphthyl, anthracenyl, 1-butenyl, 2-butenyl, pentenyl, hexenyl, tolyl, xylenyl, diethylphenyl, ethyltolyl, acetyl, benzoyl, toluyl, dimethoxyphosphoryl, dimethoxythiophosphoryl, diethoxyphosphoryl, diethylthiophosphoryl, dibutoxyphosphoryl, dimethylphosphoryl, dimethylthiophosphoryl, diethylphosphoryl, methylphenylphosphoryl, methylethylphosphoryl, ethylphenylphosphoryl, and 2-benzothiazolyl.

Examples of $R_1$ and $R_2$ when the radicals have substituents are 2-chloroethyl, 2-hydroxyethyl, 2-chloropropyl, 3-chloropropyl, 4-bromobutyl, 4-chlorophenyl, 2-bromophenyl, p-bromobenzyl, 3-chloropropenyl, 5-chloro(2-benzothiazolyl), 6-ethoxy(2-benzothiazolyl), 4-fluorocyclohexyl, 3-chlorocyclohexyl, 5-nitro(2-benzothiazolyl) and 4-nitrophenyl.

Other azoles and nuclear substituted azoles besides benzothiazoles which are suitable for Y and Y' are 2-benzothiazolyl, 2-benzoxazolyl, 2-benzimidazolyl, 2-thiazolyl, 2-thiazolinyl, 2-naphthathiazolyl, 2-(4,5,6,7-tetrahydro)-benzothiazolyl, s-triazolo[3,4-b]benzothiazol-3-yl and said azoles substituted by chloro, bromo, fluoro, iodo, hydroxy, alkoxy, nitro, lower alkyl, acetyl, lower alkyl carboxyl, acetoxy, acetoxyalkyl, phenyl-carbamoyl and 2-mercapto-4,4,6-trimethyl-1[4H]pyrimidinyl.

Illustrative symmetrical disulfides which may be prepared by the process of this invention are:

Methyl thioperoxydiphosphate, ethyl thioperoxydiphosphate, propyl thioperoxydiphosphate, isopropyl thioperoxydiphosphate, n-butyl thioperoxydiphosphate, sec-butyl thioperoxydiphosphate, hexyl thioperoxydiphosphate, octyl thioperoxydiphosphate, nonyl thioperoxydiphosphate, cyclohexyl thioperoxydiphosphate, benzyl thioperoxydiphosphate, allyl thioperoxydiphosphate and O-ethyl-O'-methyl thioperoxydiphosphate.

Illustrative asymmetrical disulfides which may be prepared by the process of this invention are:

O,O-'diethylcyclohexylthiophosphorodithioate,
O,O'-di-n-butylcyclohexylthiophosphorodithioate,
O,O'-diethyl-S-phenylthiophosphorodithioate,
O,O'-di-n-butyl-S-phenylthiophosphorodithioate,
O,O'-diethylcyclohexylthiophosphorothioate,
O,O'-di-n-butylcyclohexylthiophosphorothioate,
O,O'-diethyl-S-phenylthiophosphorothioate,
O,O'-di-n-butyl-S-phenylthiophosphorothioate,
S-phenylthiodiphenylphosphinodithioate,
S-phenylthiodiethylphosphinodithioate,
S-cyclohexyldiphenylphosphinodithioate,
S-cyclohexylthiodiethylphosphinodithioate,
S-n-butylthiodiphenylphosphinodithioate,
O,O'-diethylphosphorotrithioyl-2-benzothiazole,
O,O'-dibenzylphosphorotrithioyl-2-benzothiazole,
O-cyclohexyl-O'-methylphosphorotrithioyl-2-benzothiazole,
O,O'-diisopropylphosphorotrithioyl 2-benzothiazole,
O,O'-di-n-butylphosphorotrithioyl 2-benzothiazole,
O,O'-dibenzylphosphorotrithioyl 2-benzoxazole,
O,O'-dimethylphosphorotrithioyl 2-benzothiazole,
O,O'-dipropylphosphorotrithioyl 6-nitro-2-benzothiazole
and O,O'-diethylphosphorotrithioyl 4-methyl-2-thiazole.

The phosphorotrithioyl-2-benzothiazoles of the invention are accelerators and vulcanizing agents for rubber.

The reaction takes place in the presence or absence of solvent. However, it is convenient, although not essential, to carry out the reaction in an inert solvent and to select one in which one of the products is insoluble because separation and recovery of the product is thereby made easier. Also the precipitation of one of the products serves as a driving force for the reaction which results in complete conversion of reactants and high yield of polysulfide. The recovered imide may be converted to a thioimide and reused. Solvents suitable for carrying out the process are water, carbon tetrachloride, ether, acetone, alcohol, aliphatic hydrocarbon solvent such as heptane or aromatic hydrocarbon solvent such as benzene or toluene.

Another feature of this process is that it can be conducted at moderate temperature. In fact, room temperature is sufficient. Generally, the reaction is conducted between 20°–100° C. The optimum temperature is determined by a number of factors such as reaction rate, boiling point of the solvent used, solubility of reactants or products, or stability of the products. In certain cases, higher reaction temperature may be used when the products are sufficiently stable.

The following specific embodiments are illustrative of the wide variety of disulfides which are produced via this process.

DESCRIPTION OF PREFERRED EMBODIMENTS

EXAMPLE 1

1,3-PROPYLENE BIS(PHENYLDISULFIDE)

2.7 Grams (0.025 mole) of 1,3-dimercaptopropane are added to 10.3 grams (0.025 mole) of N-phenylthiosuccinimide in 150 ml of benzene at room temperature (~25° C.). After stirring for one hour, 4.9 grams of succinimide (m.p. 122° C.) are recovered by filtration. Evaporation of the solvent gives an oil identified as 1,3-propylene bis(phenyl disulfide).

EXAMPLE 2

PHENYL DISULFIDE 5.5 Grams (0.05 mole) of thiophenol are stirred with 10.2 grams (0.05 mole) of N-(phenylthio)maleimide in 150 ml of benzene at room temperature for one hour. The benzene is removed from the reaction mixture by evaporation and the residue is added to 200 ml of methanol. A white solid forms upon contact with the methanol which is recovered by filtration. The solid recovered is 9.2 grams (84% yield) of phenyl disulfide. Recrystallized from methanol, the product melts sharply at 60° C.

EXAMPLE 3

2-(tert-BUTYLDITHIO)BENZOTHIAZOLE 11.8 Grams (0.05 mole) of N-(tert-butylthio)phthalimide and 8.5 grams (0.05 mole) of 2-mercaptobenzothiazole in 200 ml of benzene are stirred at 70° C. for six hours. The reaction mixture is cooled and filtered to obtain 7.1 grams of phthalimide (white solid, m.p. 231° C.). The benzene is stripped from the filtrate by evaporation to give a solid residue. The residue recrystallized from methanol gives 9.3 grams of 2-(tert-butyldithio)benzothiazole, m.p. 80.0°–80.5° C. Another 3.0 grams of product are obtained upon concentration of the alcoholic filtrate.

EXAMPLE 4

PHENYL DISULFIDE

This example illustrates that the disulfides may be prepared without the use of solvent. 12.1 Grams (0.11 mole) of thiophenol are added in one portion to 20.7 grams of N-phenylthio succinimide. The reaction container is blanketed with nitrogen to reduce the presence of moisture. The temperature of the reaction mixture rises from 23° C. to 58° C. After stirring for 15 minutes, 400 ml of water (at 70°–75° C.) are added and the mixture stirred 10 more minutes. The slurry is cooled and then filtered to recover 21.0 grams (96% yield) of phenyl disulfide. Recrystallized from methanol, the product melts at 59° C.

EXAMPLE 5

ALLYL PHENYL DISULFIDE 7.4 Grams (0.1 mole) of 2-propene-1-thiol(allyl mercaptan) are added to 20.0 grams (0.1 mole) of N-phenylthiosuccinimide in 300 ml of benzene and are stirred for eight hours at room temperature. 8.5 Grams of succinimide (m.p. 123°–124° C.) are recovered by filtration. The filtrate is washed with 0.1N sodium hydroxide and then with water. The washed filtrate is dried over sodium sulfate, filtered to remove the sodium sulfate and evaporated at reduced pressure to yield 17.0 grams of crude allyl phenyl disulfide. The crude allyl phenyl disulfide is distilled and 11.8 grams of pure product are collected at 75°–79° C. and 0.5 mm Hg.

EXAMPLE 6

1,6-BIS PHENYL n-HEXYL DISULFIDE

This example illustrates the preparation of bis-alkyl disulfides. 1.12 Grams (0.01 mole) of thiophenol are added to 2.21 grams (0.005 mole) of 1,6-bis(N-thiophthalimido)-n-hexane in 80 ml of benzene. The reaction mixture is heated at 60° C. for three hours and then allowed to cool and stand overnight at room temperature. The mixture is filtered to remove phthalimide. The filtrate is extracted with several 20 ml portions of 0.1N NaOH and then extracted with 20 ml of water. The benzene solution is filtered to remove traces of water and the benzene evaporated to yield an amber liquid identified by NMR analysis as 1,6-bis phenyl n-hexyl disulfide.

EXAMPLE 7

BENZYL-tert-OCTYL TRISULFIDE 0.372 Grams (0.003 mole) of benzyl mercaptan are added to 0.809 grams (0.0025 mole) of N-tert-octyldithiophthalimide in 25 ml of benzene. The reaction mixture is stirred for 48 hours at room temperature. The mixture is washed with 3 portions of 0.1N NaOH and one portion of water to remove the phthalimide and then is dried over sodium sulfate. The benzene is evaporated at room temperature to yield 0.752 grams of an amber oil (100% yield). Upon standing, solids (phthalimide) formed in the crude product. The product is extracted with petroleum ether leaving behind the solids. The ether is evaporated to recover the purified product. The product is identified by NMR analysis as benzyl-tert-octyl trisulfide.

EXAMPLE 8

BENZOYLCYCLOHEXYL DISULFIDE 13.1 Grams (0.05 mole) of N-(cyclohexylthio)phthalimide and 6.9 grams (0.05 mole) of benzoyl thiol(thiobenzoic acid) in 150 ml of heptane are stirred overnight at room temperature. The precipitate is recovered by filtration, washed with carbon tetrachloride and dried. 7.3 Grams of phthalimide (m.p. 234° C.) are obtained. The solvent is removed from the filtrate by evaporation under reduced pressure. 12 Grams (95% yield) of product, a light brown liquid, are obtained. The identity of the benzoylcyclohexyl disulfide is confirmed by GLC and NMR analyses. Analysis gives 25.51% sulfur compared to 25.45% sulfur calculated for $C_{13}H_{16}OS_2$. Similarly, except N-(2-benzothiazolylthio)phthalimide is one reactant, there is obtained benzoyl-2-benzothiazolyl disulfide.

EXAMPLE 9

O,O'-DIETHYLCYCLOHEXYLTHIOPHOSPHORODITHIOATE 18.6 Grams (0.1 mole) of O,O'-diethyl-S-hydrogen phosphorodithioate are added to 26 grams (0.1 mole) of N(cyclohexylthio)phthalimide in 300 ml of heptane at 70° C. After stirring for two hours at 70° C., 14.7 grams of phthalimide (white solid, m.p. 233°–234° C.) are recovered by filtration. The filtrate is evaporated to yield 28.0 grams (93% yield) of a yellow liquid which is identified as the desired disulfide. Similarly, except N-(2-benzothiazolylthio)-phthalimide is one reactant, there is obtained O,O'-diethylphosphorotrithioyl 2-benzothiazole.

EXAMPLE 10

O,O'-DI(2-BUTYL)CYCLOHEXYLTHIOPHOSPHORODITHIOATE

O,O'-Di(2-butyl)-S-hydrogen phosphorodithioate, 0,055 moles (14.2 grams of 94% assay), is added at room temperature to a stirred solution of N-(cyclohexylthio)phthalimide, 0.05 moles, 13.1 grams, in 100 ml of benzene. The mixture is heated at 60° C. for three hours. After cooling to 5°, less than the theoretical quantity of phthalimide is recovered by filtration. The mixture is reheated at 60° C. for four hours, cooled and filtered to recover additional phthalimide. The filtrate is washed four times with 10 ml portions of 10% NaCl/10% $Na_2CO_3$ solution and three times with 10 ml portions of water. After drying over $Na_2SO_4$, the benzene is evaporated at room temperature. The residue is dissolved in 25 ml of heptane, filtered to remove small amounts of undissolved material, and the filtrate evaporated. O,O'-Di(2-butyl)-cyclohexylthiophosphorodithioate, a light yellow liquid, is recovered in 93% yield (16.5 grams). Chemical analysis gives 48.53%C, 8.16H, 8.69%P and 26.79%S compared to 47.3%C, 8.15%H, 8.71%P and 27.0%S calculated for $C_{14}H_{29}O_2PS_3$. Similarly, except N-(2-benzothiazolylthio)phthalimide is one reactant, there is obtained O,O'-di(2-butyl)phosphorotrithioyl 2-benzothiazole.

EXAMPLE 11

O,O'-DI(n-HEXYL)BENZYLTHIOPHOSPHORODITHIOATE

O,O'-Di(n-hexyl)-S-hydrogen phosphorodithioate, 0.0165 moles, (5.9 grams of 84% assay), is added dropwise to a stirred solution at 60° C. of N-(benzylthio)phthalimide 0.015 moles, 4.04 g, in 100 ml of benzene. The mixture is stirred overnight at room temperature, cooled to 5° C. and filtered to remove phthalimide by-product. The filtrate is washed twice with 25 ml portions of 10% NaCl/10% $Na_2CO_3$ solutions, and once with a 25 ml portion of water. After drying over $Na_2SO_4$, the benzene is evaporated in a rotary evaporator. O,O'-Di(n-hexyl)benzylthiophosphorodithioate is recovered in about 66% yield (4.16 grams). Chemical analysis gives 56.7%C, 7.75%H, 6.97%P and 22.8%S compared to 54.3%C, 7.89%H, 7.39%P and 22.9%S calculated for $C_{19}H_{33}O_2PS_3$. Similarly, except N-(2-benzothiazolylthio) phthalimide is one reactant, there is obtained O,O'-di(n-hexyl)phosphorotrithioyl-2-benzothiazole.

EXAMPLE 12

ACETYLCYCLOHEXYL DISULFIDE

Thioacetic acid, 0.444 moles, 3.35 grams, is reacted with N-(cyclohexylthio)phthalimide in 100 ml of benzene and the product recovered following a procedure similar to Example 11. Acetylcyclohexyl disulfide, an amber oil, is recovered in 98% yield (7.5 grams). Analysis gives 51.27%C, 7.41%H and 31.78%S compared to 50.6%C, 7.38%H and 33.7%S calculated for $C_8H_{14}OS_2$.

Other asymmetrical disulfides of the invention are: Benzoyl 2-benzothiazolyl disulfide, benzoyl 6-nitro-2benzothiazolyl disulfide, benzoyl 4-methyl-2-thiazolyl disulfide, benzoyl 2-benzoxazolyl disulfide, acetyl 2-benzothiazolyl disulfide, acetyl 5-chloro-2-benzothiazolyl disulfide, acetyl 4,5-dimethyl-2-thiazolyl disulfide, acetyl 2-benzoxazolyl disulfide, benzoyl ethyl disulfide, benzoyl methyl disulfide, benzoyl propyl disulfide, benzoyl cyclopentyl disulfide, benzoyl cyclohexyl disulfide, benzoyl phenyl disulfide, benzoyl benzyl disulfide, acetyl methyl disulfide, acetyl propyl disulfide, acetyl n-butyl disulfide, acetyl phenyl disulfide, acetyl benzyl disulfide, acetyl benzoyl disulfide, O,O'-dimethyl benzoylphosphorotrithioate, O,O'-diethyl benzoylphosphorotrithioate, O,O'-diisopropyl benzoylphosphorotrithioate, O,O'-di-n-butyl benzoylphosphorotrithioate, O,O'-dimethyl acetylphosphorotrithioate, O,O'-diethyl acetylphosphorotrithioate, O,O'-diisopropyl acetylphosphorotrithioate, and O,O'-di-n-butyl acetylphosphorotrithioate.

Phosphorotrithioyl-2-azoles and especially O,O'-dialkyl phosphorotrithioyl 2-benzothiazoles are potent accelerators and vulcanizing agents for the vulcanization of rubber and are used in the same manner as conventional accelerators or vulcanizing agents by incorporation into the rubber composition and heating to effect vulcanization.

2-(Isopropyldithio)benzimidazole, m.p. 182°–185° C., is a potent inhibitor of prevulcanization of vulcanizable rubber compositions, especially sulfur vulcanizable rubber compositions, which compound is used in the same manner as conventional prevulcanization inhibitors by incorporation into the rubber composition.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. 2-(Isopropyldithio)benzimidazole.

* * * * *

UNITED STATES PATENT OFFICE
CERTIFICATE OF CORRECTION

PATENT NO. : 4,119,780
DATED : October 10, 1978
INVENTOR(S) : Alfred Bay Sullivan It is certified that error appears in the above-identified patent and that said Letters Patent are hereby corrected as shown below:

Column 1, end of first paragraph (following 1972):

"This invention relates to the manufacture of organic polysulfides. More particularly, it concerns the preparation of organic polysulfides from sulfenamides."

should be added.

Column 3, line 59: "ot" should be --of--.

Column 5, line 22: "acyclcic" should be --acyclic--.

Column 10, line 6: "0.444" should be --0.044--.

Signed and Sealed this

Twenty-fourth Day of April 1979

[SEAL]

Attest:

RUTH C. MASON
Attesting Officer

DONALD W. BANNER
Commissioner of Patents and Trademarks